United States Patent
Rademacher et al.

(10) Patent No.: US 8,008,377 B2
(45) Date of Patent: Aug. 30, 2011

(54) MODIFIED ASPHALT BINDERS AND ASPHALT PAVING COMPOSITIONS

(75) Inventors: Christine Rademacher, Akron, OH (US); Daniel Graves, Canal Fulton, OH (US); Herb Wissel, Indianapolis, IN (US); Timothy Reece, Indianapolis, IN (US)

(73) Assignees: Firestone Polymers, LLC, Akron, OH (US); Heritage Research Group, Indianapolis, IN (US)

( * ) Notice: Subject to any disclaimer, the term of this patent is extended or adjusted under 35 U.S.C. 154(b) by 0 days.

(21) Appl. No.: 12/665,815

(22) PCT Filed: Jun. 19, 2008

(86) PCT No.: PCT/US2008/007629
§ 371 (c)(1),
(2), (4) Date: Feb. 26, 2010

(87) PCT Pub. No.: WO2008/156804
PCT Pub. Date: Dec. 24, 2008

(65) Prior Publication Data
US 2010/0324179 A1    Dec. 23, 2010

Related U.S. Application Data

(60) Provisional application No. 60/936,410, filed on Jun. 20, 2007.

(51) Int. Cl.
*C08L 95/00* (2006.01)

(52) U.S. Cl. ......................................................... 524/68
(58) Field of Classification Search ..................... 524/68
See application file for complete search history.

(56) References Cited

U.S. PATENT DOCUMENTS

| | | | |
|---|---|---|---|
| 3,275,586 A | 9/1966 | Wurstner et al. | |
| 4,145,322 A | 3/1979 | Maldonado et al. | |
| 4,437,896 A | 3/1984 | Partanen | |
| 5,990,206 A | 11/1999 | Tanaka et al. | |
| 6,569,351 B1 | 5/2003 | Baumgardner et al. | |
| 6,713,539 B2 * | 3/2004 | Guo et al. | 524/68 |
| 2004/0152805 A1 * | 8/2004 | Buras | 524/59 |

FOREIGN PATENT DOCUMENTS

| | | |
|---|---|---|
| JP | 51149312 A | 12/1976 |
| WO | 2006041560 A1 | 4/2006 |

OTHER PUBLICATIONS

International Report on Patentability dated Jan. 7, 2010, International Application No. PCT/US2008/007629.
International Search Report dated Feb. 4, 2009, International Application No. PCT/US2008/007629.
Synlett, Ed., Polshettiwar, V., "Phosphorus Pentasulfide (P4S10)", Issue 12, Oct. 1, 2004, pp. 2245-2246.

* cited by examiner

*Primary Examiner* — Peter Szekely
(74) *Attorney, Agent, or Firm* — Meredith E. Hooker; Arthur M. Reginelli

(57) ABSTRACT

A process for preparing a modified asphalt binder composition, the process comprising mixing asphalt, an unsaturated polymer, and an organothionating agent to form a modified asphalt composition.

9 Claims, 1 Drawing Sheet

MODIFIED ASPHALT BINDERS AND ASPHALT PAVING COMPOSITIONS

This invention claims the priority of International Application Serial No. PCT/US2008/007629, filed on Jun. 19, 2008, and U.S. Provisional Patent Application Ser. No. 60/936,410, filed on Jun. 20, 2007, which are incorporated herein by reference.

FIELD OF THE INVENTION

One or more embodiments of the present invention are directed toward modified asphalt binder compositions that are prepared by employing an organothionating agent and polymer, as well as asphalt paving compositions prepared using these binder compositions.

BACKGROUND OF THE INVENTION

Asphalt paving compositions, which include a mixture of asphalt binder and aggregate, have long been employed in the manufacture of pavements. The long-standing technological challenge with these pavements has been their behavior at extreme temperatures. That is, at high temperatures, the pavements become soft; and at low temperatures, the pavements are brittle.

For decades, additives have been employed to alleviate the problems experienced at extreme temperatures. For example, polymers have been added to asphalt binder compositions. U.S. Pat. No. 4,145,322 teaches polymer-modified bitumen compositions that include elastomers (e.g., polyisoprene, butyl rubber, SBR rubber) that can be employed to improve the mechanical properties of, the bitumens, especially the elastomeric properties. And, the use of particular block copolymers of styrene and diene monomer in these bitumen compositions provides compositions having desirable mechanical properties even at low temperatures.

In a similar fashion, JP 51-149312 (1976) teaches modified asphalt compositions that include a phosphorus compound, such as phosphorus pentoxide, polyphosphoric acid, or thionating agents. It is suggested that these phosphorus compounds can modify the asphalt because they bond to the asphaltene in the asphalt to further strengthen the gel structure. In order to overcome dispersibility and handling issues associated with these phosphorus compounds, the phosphorus compounds are mixed with petroleum compositions, and the mixture is added to the asphalt composition. The petroleum compositions are characterized by an ignition point of 150° C. or higher and include 0.5-40% asphaltenes. The phosphorus compounds can be included in the petroleum composition in an amount from 0.5 to 50 weight percent, and the amount of phosphorus compound added to the asphalt to be modified may be from 0.2 to 5.0 weight percent.

U.S. Pat. No. 6,569,351 teaches polymer modified asphalt compositions prepared by combining an accelerator-gel additive with polymer and asphalt, and curing the polymer-modified asphalt at a temperature between 200° F. and 500° F. The accelerator-gel additives include 2-75% accelerator, 25-88% processing oil, and 0.5-10% clay. The accelerator may include sulfur, 4,4'-dithiodimorpholine, thiazole derivatives, dithiocarbanates, thionating agents, phosphorus pentoxide, zinc stearate, ammonium stearate, sodium hydroxide, potassium hydroxide, calcium hydroxide, aluminum oxide, or combinations of these or other vulcanizers or accelerators. The accelerator-gel additive may be added to concentrates between approximately 1-25% polymer.

U.S. Pat. No. 5,990,206 teaches a mixture of polymer and phosphorus compound (modifier composition) for use in asphalt compositions. The polymer may include a rubber-base polymers (modifier) and/or a resin-based polymer (modifier). The phosphorus compounds may include phosphoric anhydride ($P_2O_5$), polyphosphoric acid, orthophosphoric acid, phosphorus oxytrichloride ($POCl_3$), phosphorus trichloride ($PCl_3$), and thionating agents ($P_2S_5$). The mixture may contain from about 0.1 to about 10% by weight of the phosphorus compound, and asphalt compositions containing from 0.1 to 30% by weight of the polymer/phosphorus compound blend (modifier composition) may be prepared. It is believed that the inorganic phosphorus compound functions as a crosslinking agent between the rubber-base and/or resin-base modifier, and a higher order network structure (asphaltene) in the asphalt, and is useful to strengthen the gel structure in the asphalt.

SUMMARY OF THE INVENTION

One or more embodiments of the present invention provide a process for preparing a modified asphalt binder composition, the process comprising mixing asphalt, an unsaturated polymer, and an organothionating agent to form a modified asphalt composition.

One or more embodiments of the present invention also provide a process for preparing a modified asphalt binder composition, the process comprising mixing asphalt binder, polymer, and an organothionating agent to form a modified asphalt composition, where the weight ratio of polymer to the organothionating agent is at least 0.5:1 and less than 8:1.

One or more embodiments of the present invention further provide a process for preparing a modified asphalt binder composition the process comprising introducing an polymer to an asphalt binder, and introducing an organothionating agent to an asphalt binder, where said step of introducing the organothionating agent to the asphalt includes adding an organothionating agent composition that includes less 5% by weight hydrocarbon material.

One or more embodiments of the present invention still further provide a method for forming a modified asphalt binder composition, the method comprising preparing an organothionating agent-binder concentrate by introducing and mixing an organothionating agent and asphalt binder, where the organothionating agents-binder concentrate includes greater than 0.5 parts by weight organothionating agents per 100 parts by weight asphalt, preparing a polymer-binder concentrate by introducing and mixing polymer and asphalt binder, where the polymer-binder concentrate includes greater than 5 parts by weight polymer per 100 parts by weight asphalt, and introducing and mixing the organothionating agent-binder concentrate with the polymer-binder concentrate to form a modified asphalt binder composition.

One or more embodiments of the present invention also provide a modified asphalt binder composition comprising the combination or the reaction product of an asphalt, an organothionating agent, and an unsaturated polymer.

One or more embodiments of the present invention also provide a modified asphalt binder composition prepared by a process comprising introducing and mixing an asphalt, an organothionating agent, and polymer, where the weight ratio of the polymer to the organothionating agents is at least 0.5:1 and less than 8:1.

DETAILED DESCRIPTION OF ILLUSTRATIVE EMBODIMENTS

Figure 1:
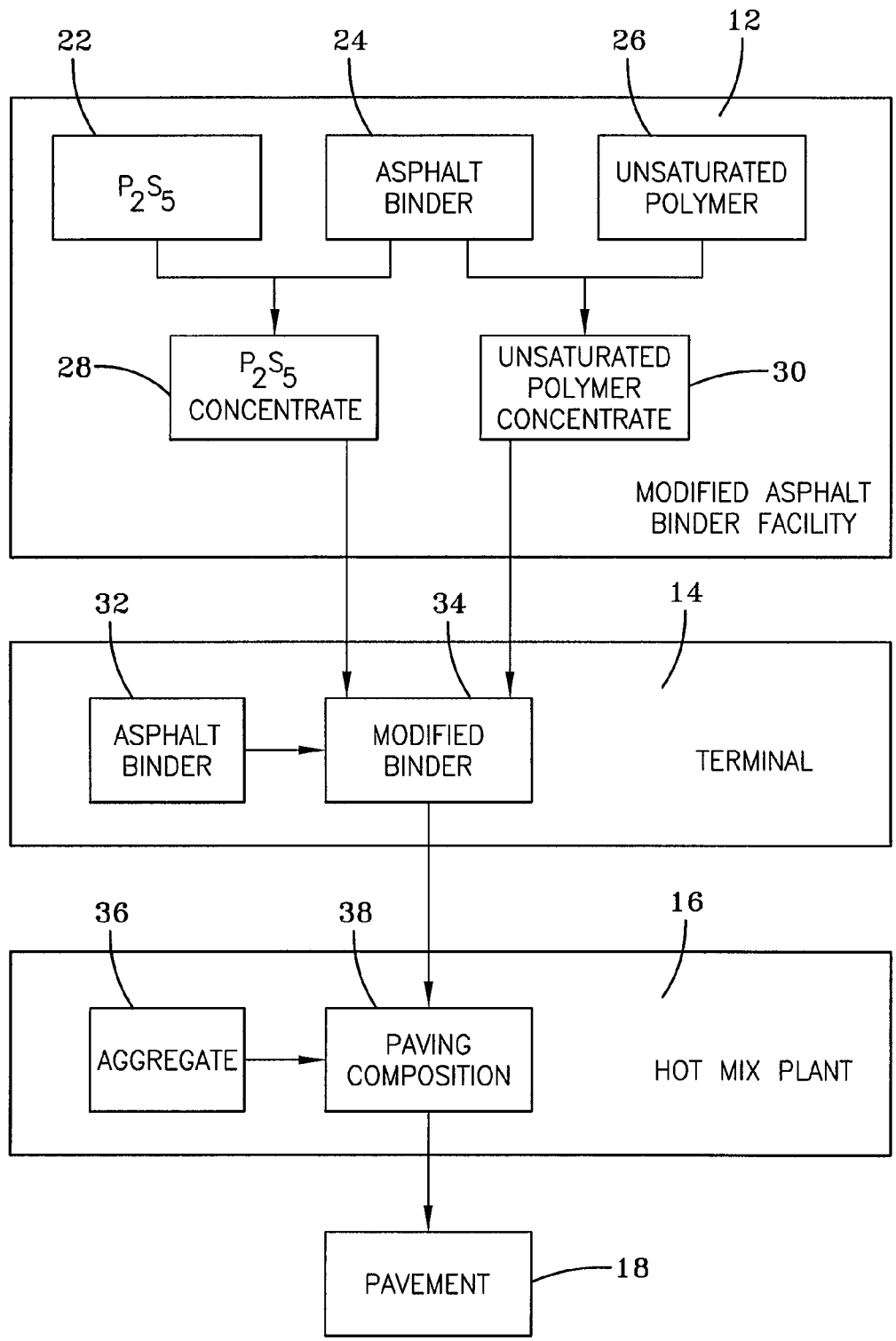
FIG. 1 is a flow chart showing a particular embodiment of the present invention.

One or more embodiments of the present invention provides a method for forming a modified asphalt binder composition that is useful for preparing asphalt paving compositions. In one or more embodiments, the modified asphalt binder composition may be formed by introducing and mixing an asphalt binder, a polymer, and an organothionating agent. The modified asphalt binder composition may be combined with aggregate to form an asphalt paving composition. In particular embodiments, the asphalt paving composition can be formed into pavements.

The term "asphalt binder" is used as understood by those skilled in the art and is consistent with the meaning provided by AASHTO M320. Where asphalt binder has been combined with aggregate, the term "asphalt paving composition" is employed. As used within this specification, the terms "asphalt" and "asphalt binder" may be used synonymously. The asphalt binder material may be derived from any asphalt source, such as natural asphalt, rock asphalt, produced from tar sands, or petroleum asphalt obtained in the process of refining petroleum. The asphalt binder may be selected from those currently graded by AASHTO M320 and ASTM D-6373, including Performance Graded Asphalt Binders. In other embodiments, asphalt binders may include a blend of various asphalts not meeting any specific grade definition. This includes air-blown asphalt, vacuum-distilled asphalt, steam-distilled asphalt, cutback asphalt or roofing asphalt. Alternatively, gilsonite, natural or synthetic, used alone or mixed with petroleum asphalt, may be selected. Synthetic asphalt mixtures suitable for use in the present invention are described, for example, in U.S. Pat. No. 4,437,896. In one or more embodiments, asphalt includes petroleum derived asphalt and asphaltic residual. These compositions may include asphaltenes, resins, cyclics, and saturates. The percentage of these constituents in the overall asphalt binder composition may vary based on the source of the asphalt.

Asphaltenes include black amorphous solids containing, in addition to carbon and hydrogen, some nitrogen, sulfur, and oxygen. Trace elements such as nickel and vanadium may also be present. Asphaltenes are generally considered as highly polar aromatic materials of a number average molecular weight of about 2000 to about 5000 g/mol, and may constitute about 5 to about 25% of the weight of asphalt.

Resins (polar aromatics) include dark-colored, solid and semi-solid, very adhesive fractions of relatively high molecular weight present in the maltenes. They may include the dispersing agents of peptizers for the asphaltenes, and the proportion of resins to asphaltenes governs, to a degree, the sol- or gel-type character of asphalts. Resins separated from bitumens may have a number average molecular weight of about 0.8 to about 2 kg/mol but there is a wide molecular distribution. This component may constitute about 15 to about 25% of the weight of asphalts.

Cyclics (naphthene aromatics) include the compounds of lowest molecular weight in bitumens and represent the major portion of the dispersion medium for the peptized asphaltenes. They may constitute about 45 to about 60% by weight of the total asphalt binder, and may be dark viscous liquids. They may include compounds with aromatic and naphthenic aromatic nuclei with side chain constituents and may have molecular weights of 0.5 to about 9 kg/mol.

Saturates include predominantly the straight- and branched-chain aliphatic hydrocarbons present in bitumens, together with alkyl naphthenes and some alkyl aromatics. The average molecular weight range may be approximately similar to that of the cyclics, and the components may include the waxy and non-waxy saturates. This fraction may from about 5 to about 20% of the weight of asphalts.

In these or other embodiments, asphalt binders may include bitumens that occur in nature or may be obtained in petroleum processing. Asphalts may contain very high molecular weight hydrocarbons called asphaltenes, which may be soluble in carbon disulfide, pyridine, aromatic hydrocarbons, chlorinated hydrocarbons, and THF. Asphalts or bituminous materials may be solids, semi-solids or liquids.

In one or more embodiments, the asphalt binders, prior to modification (i.e., prior to combination with unsaturated polymer or $P_2S_5$), may be characterized by a PG rating of at least PG 64-22, in other embodiments at least PG 52-28, and in other embodiments at least PG 52-34. It should be noted that each of these exemplary asphalt binders have a temperature performance range of 86° C. While the selection of these asphalt binders may be advantageous desirable and certain embodiments, practice of the present invention advantageously allows for the use of a base asphalt binder with a lower temperature range because this lower temperature range can be upgraded through practice of the present invention. For example, a PG 64-16, PG 58-22, or PG 52-28 can be modified to increase its temperature range. As those skilled in the art appreciate, PG rating refers to Super Pave (Superior Performing Pavements) Performance Graded (PG) binder specifications as developed in the United States through research funded by the Association of American Highway and Transportation Officials (AASHTO M320).

In one or more embodiments, the polymers may be characterized by a glass transition temperature (Tg), as measured by DSC analysis, of less than 20° C., in other embodiments less than 0° C., in other embodiments less than −20° C., in other embodiments less than −35° C., and in other embodiments from about −90° C. to about −20° C.

In one or more embodiments, the polymer employed is an unsaturated polymer. In one or more embodiments, unsaturated polymers include hydrocarbon-based polymers that have a degree or amount of unsaturation that may be quantified based upon the number of double bonds (either backbone or pendant non-conjugated double bonds) per total number of carbon atoms within a polymer (including pendant carbon atoms). For example, in one or more embodiments, the unsaturated polymers include at least 5 double bonds, in other embodiments at least 7 double bonds, in other embodiments at least 12 double bonds, and in other embodiments at least 16 double bonds per 100 carbon atoms in the polymer. In these or other embodiments, the unsaturated polymers include from about 7 to about 25 double bonds, in other embodiments from about 10 to about 20 double bonds, and in other embodiments from about 12 to about 18 double bonds per 100 carbon atoms.

Unsaturated polymers include those polymers that include backbone, pendant, or both backbone and pendant unsaturation (i.e., non-conjugated double bonds). For example, mer units deriving from the 1,2-polymerization mechanism of 1,3-butadiene, or mer units deriving from the 3,4 polymerization mechanism of isoprene, are pendant, vinyl units. The amount of pendant non-conjugated double bonds may be quantified based on the vinyl percentage of the mer units containing unsaturation. For example, a polymer having 30% vinyl content refers to a polymer in which 30% of unsaturated mer units are pendant non-conjugated double bonds. In one or more embodiments, the unsaturated polymers employed in practicing the present invention include zero or only negligible vinyl content. In other embodiments, unsaturated polymers include low vinyl content (e.g., 1 to about 10%); in other embodiments, they include medium vinyl content (e.g., 11 to 40%); and in other embodiments, they include high vinyl content (e.g., greater than 40%).

In one or more embodiments, the unsaturated polymers may also include mer units that do not include non-conjugated double bonds. For example, mer units deriving from the polymerization of comonomer, such as styrene, do not include non-conjugated double bonds. In one or more embodiments, the unsaturated polymers may include from about 0% to about 55% mer units (i.e., based upon moles), in other embodiments from about 3 to about 50% mer units, and in other embodiments from about 10 to about 45% mer units deriving from monomer that does not provide non-conjugated double bonds (e.g., styrene).

In one or more embodiments, the unsaturated polymers may be characterized by a melt index (ASTM D-1238; 2.16 kg load @ 190° C.) of less than 1,000 dg/min, in other embodiments less than 500 dg/min, in other embodiments less than 50 dg/min, in other embodiments less than 20 dg/min, in other embodiments less than 10 dg/min, and in other embodiments less than 1 dg/min. In these or other embodiments, the unsaturated polymers may have a melt index of between 3 and 15 dg/min, and other embodiments between 4 and 12 dg/min.

In one or more embodiments, the unsaturated polymers may be characterized by a number average molecular weight ($M_n$) of from about 10 to about 1,000 kg/mol, in other embodiments from about 40 to about 500 kg/mol, and in other embodiments from about 80 to about 200 kg/mol. In these or other embodiments, the unsaturated polymers may also be characterized by a weight average molecular weight ($M_w$) of from about 10 to about 4,000 kg/mol, in other embodiments from about 40 to about 2,000 kg/mol, and in other embodiments from about 80 to about 800 kg/mol. In one or more embodiments, the unsaturated polymers may be characterized by a molecular weight distribution of from about 1.1 to about 5, in other embodiments from about 1.5 to about 4.5, and in other embodiments from about 1.8 to about 4.0. Molecular weight can be determined by gel permeation chromatography (GPC) calibrated with polystyrene standards and adjusted for the Mark-Houwink constants for the polymer in question.

The hydrocarbon based unsaturated polymers may be linear, branched, or coupled polymers. Types of hydrocarbon polymers may include both natural and synthetic polymers. Useful synthetic polymers may include polydienes or polydiene copolymers with non-diene comonomer (e.g., styrene). The copolymers may include block and random copolymers. The coupled polymers may include linearly coupled polymers (e.g. di-coupled polymers) or raidally coupled polymers (e.g. tri-coupled or, tetra-coupled penta-coupled, hexa-coupled etc.). Exemplary polydienes include polybutadiene and polyisoprene. Exemplary copolymers may include random styrene-butadiene rubber, styrene-butadiene block copolymer, styrene-butadiene-styrene block copolymer, random styrene-isoprene, styrene-isoprene block copolymer, styrene-isoprene-butadiene block copolymer, random styrene-isoprene-butadiene, styrene-isoprene-styrene block copolymer, and chloroprene rubber. In one or more embodiments, the polymer may include a high-vinyl block copolymer as described in International Application No. PCT/US2005/028343. In one or more embodiments, the unsaturated polymers include linear or radial block copolymers wherein the block copolymers include terminal styrene blocks. For example, in the case of a radial tri-coupled polymer, each of the three radial arms of the polymer will include terminal styrene blocks. In these or other embodiments, the internal segments of the radial arms include polydiene blocks such as polybutadiene blocks. In these or other embodiments, the styrene content of these block copolymers may be from 10% to 50% by weight, in other embodiments from 15% to 45% by weight, and in other embodiments from 20% to 40% by weight.

In one or more embodiments, the polymer may include an anionically-polymerized polymer. In other embodiments, the polymer may be produced by coordination catalysis such as by using cobalt-based, nickel-based, or lanthanide-based coordination systems.

In one or more embodiments, the polymer may include a polydiene and/or polydiene copolymer including a polar group. These polar groups may be positioned pendant to the polymer backbone and/or at the terminus of the polymer backbone. In one or more embodiments, the polar group may include a carbonyl group such as a carboxylic acid group or an anhydride group, hydroxyl group, amino group, amido group, carbamate group, silicon-containing, metal-containing groups, phosphorus-containing groups and the like.

In one or more embodiments, the polymer may be introduced to the asphalt compositions in several forms. For example, the polymer can be added as a crumb, as ground polymer, as pellets, as molten polymer, or as a liquid polymer.

In one or more embodiments, organothionating agents include those compounds that contain a sulfur atom doubly bonded to a phosphorus atom, the phosphorus atom itself is bonded to at least two other (or additional) sulfur atoms, and an organic group is directly attached to the phosphorus atom or indirectly attached via a heteroatom. In one or more embodiments, the organothionating agents may be represented by the formula:

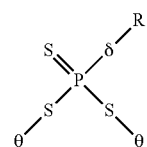

where R is a monovalent organic group, δ is a bond or a heteroatom, and θ is an inorganic moiety, and organic moiety, or combination thereof.

In one or more embodiments, monovalent organic groups include hydrocarbyl groups or substituted hydrocarbyl groups such as, but not limited to alkyl, cycloalkyl, substituted cycloalkyl, alkenyl, cycloalkenyl, substituted cycloalkenyl, aryl, allyl, substituted aryl, aralkyl, alkaryl, and alkynyl groups, with each group preferably containing from 1 carbon atom, or the appropriate minimum number of carbon atoms to form the group, up to 20 carbon atoms. These hydrocarbyl groups may contain heteroatoms such as, but not limited to, nitrogen, boron, oxygen, silicon, selenium, sulfur, and phosphorus atoms.

In particular embodiments, the monovalent organic groups may include metal atoms and therefore may be referred to as monovalent organometallic groups. In one or more embodiments, the monovalent organic group may include a metallocene. Exemplary metallocenes include titanocenes, ferrocenes, and zirconocenes.

In one or more embodiments, δ, which may be a heteroatom, may include, but is not limited to, nitrogen, boron, oxygen, silicon, selenium sulfur, and phosphorus atoms.

In one or more embodiments, the organothionating agent is a cyclic thionating agent, where the phosphorus atom to which a sulfur is doubly bonded is a member of a ring structure. In particular embodiments, the cyclic thionating agents may be represented by the formula

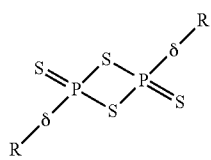

where each R is independently a monovalent organic group and each δ is independently a bond or a heteroatom.

In one or more embodiments, at least one R is an aryl group. In other embodiments, each R is independently an aryl group.

In one or more embodiments, aryl groups include phenyl, substituted phenyl, biphenyl, substituted biphenyl, heterocyclic aryl, substituted heterocyclic aryl, bicyclic aryl, substituted bicyclic aryl, polycyclic aryl, and substituted polycyclic aryl groups. Substituted aryl groups include those where a hydrogen atom is replaced by a monovalent organic group such as a hydrocarbyl group.

Exemplary substituted phenyl groups include 2-methylphenyl, 3-methylphenyl, 4-methylphenyl, 2,3-dimethylphenyl, 3,4-dimethylphenyl, 2,5-dimethylphenyl, 2,6-dimethylphenyl, and 2,4,6-trimethylphenyl (also called mesityl).

Exemplary heterocyclic aryl groups include 2-thienyl, 3-thienyl, 2-furyl, 3-furyl, N-methyl-2-pyrrolyl, N-methyl-3-pyrrolyl, N-methyl-2-imidazolyl, 1-pyrazolyl, 2-pyridyl, 3-pyridyl, 4-pyridyl, pyrazinyl, 2-pyrimidinyl, 3-pyridazinyl, 3-isothiazolyl, 3-isoxazolyl, 3-furazanyl, and 2-triazinyl groups.

Exemplary bicyclic or polycyclic aryl groups include 1-naphthyl, 2-napthyl, 9-anthryl, 9-phenanthryl, 2-benzo[b]thienyl, 3-benzo[b]thienyl, 2-naphtho[2,3-b]thienyl, 2-thianthrenyl, 1-isobenzofuranyl, 2-xanthenyl, 2-phenoxathiinyl, 2-indolizinyl, N-methyl-2-indolyl, N-methyl-indazol-3-yl, N-methyl-8-purinyl, 3-isoquinolyl, 2-quinolyl, 3-cinnolinyl, 2-pteridinyl, N-methyl-2-carbazolyl, N-methyl-β-carbolin-3-yl, 3-phenanthridinyl, 2-acridinyl, 1-phthalazinyl, 1,8-naphthyridin-2-yl, 2-quinoxalinyl, 2-quinazolinyl, 1,7-phenanthrolin-3-yl, 1-phenazinyl, N-methyl-2-phenothiazinyl, 2-phenarsazinyl, and N-methyl-2-phenoxazinyl.

In one or more embodiments, R is a hydrocarbyloxy phenyl group, and the organothionating agent may be defined by the formula

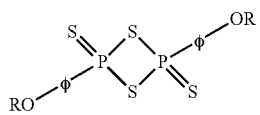

where φ is a phenyl group or substituted phenyl group and R is a monovalent organic group. In one or more embodiments, hydrocarbyloxy groups include those groups defined by the formula —OR, where R is a monovalent organic group (e.g. alkoxy or aryloxy groups).

In one or more embodiments, the thionating agent is the Lawesson's Reagent, which may be generically defined by the formula

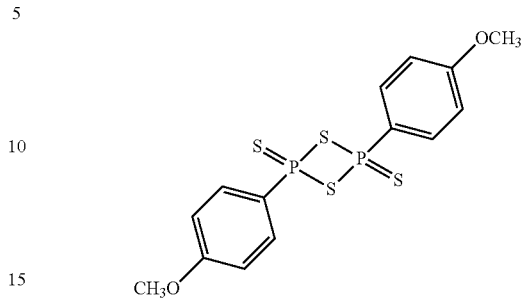

The modified asphalt binder compositions of this invention may also include those other ingredients or constituents that are commonly employed in the industry. For example, the compositions may include anti-stripping compounds.

In other embodiments, curing agents can optionally be added to the modified asphalt binder compositions of this embodiment. Curing agents may include phenolic resins and elemental sulfur. One example is a bismaleimide curing agent. Conventional amounts may be employed in practicing this invention. In one or more embodiments, the need for a curing agent, particularly sulfur, is eliminated. In other words, asphalt binder compositions of the present invention can be prepared without the addition of a curing agent and/or a sulfur-containing curative other than the thionating agents.

The asphalt binder compositions of the present invention may include from about 0.1 to about 10 parts by weight, in other embodiments from about 0.2 to about 6 parts by weight, and in other embodiments from about 0.5 to about 4 parts by weight polymer per 100 parts by weight asphalt binder. In these or other embodiments, the asphalt binder compositions of the present invention may include less than 5 parts by weight, in other embodiments less than 4 parts by weight, in other embodiments less than 3 parts by weight, in other embodiments less than 2.5 parts by weight, in other embodiments less than 2 parts by weight, in other embodiments less than 1.8 parts by weight, in other embodiments less than 1.5 parts by weight polymer per 100 parts by weight asphalt binder. In these or other embodiments, the asphalt binder compositions include at least 0.1 parts by weight, in other embodiments at least 0.5 parts by weight, in other embodiments at least 0.7 parts by weight, in other embodiments at least 1.0 parts by weight, and in other embodiments at least 1.2 parts by weight polymer per 100 parts by weight asphalt binder.

The asphalt binder compositions of the present invention may include from about 0.001 to about 20, in other embodiments from about 0.05 to about 10, in other embodiments from about 0.02 to about 5, and in other embodiments from about 0.01 to about 2 parts by weight organothionating agents per 100 parts by weight asphalt binder.

In one or more embodiments, the weight ratio of unsaturated polymer to organothionating agents within the modified asphalt binder composition may be at least 0.5:1, in other embodiments at least 0.7:1, in other embodiments at least 1:1, in other embodiments at lest 1.3:1, in other embodiments at least 1.5:1, in other embodiments at least 1.8:1, and in other embodiments at least 2.0:1. In these or other embodiments, the weight ratio of unsaturated polymer to organothionating agents is less than 8:1, in other embodiments less than 7:1, in other embodiments less than 6:1, in other embodiments less than 5:1, in other embodiments less than 4:1, and in other embodiments less than 3:1.

In those embodiments where a curative is employed, the asphalt compositions of this invention may include from about 0.1 to about 10, in other embodiments from about 0.2 to about 6, and in other embodiments from about 0.5 to about 4 parts by weight curative per 100 parts by weight asphalt. In these or other embodiments, the formation of the asphalt binder compositions of the present invention may employ less than 3 parts, in other embodiments less than 1 parts, in other embodiments less than 0.5 parts, in other embodiments less than 0.25 parts, in other embodiments less than 0.1 parts, and in other embodiments less than 0.01 parts by weight curative (e.g., free sulfur or elemental sulfur) per 100 parts by weight asphalt binder.

In one or more embodiments, the organothionating agents can be employed in the practice of the invention without the use of a polyphosphoric acid or derivative thereof. In certain embodiments, less than 1 part by weight, in other embodiments less than 0.1 parts by weight, in other embodiments less than 0.05 parts by weight, and in other embodiments less than 0.01 parts by weight polyphosphoric acid or a derivative thereof, per 100 parts by weight asphalt, is employed in practicing the invention. In one or more embodiments, no polyphosphoric acid is employed or added to the asphalt compositions. In one or more embodiments, the asphalt compositions of this invention are devoid of polyphosphoric acid or the reaction products thereof with one or more constituents of the asphalt composition.

In one or more embodiments, the asphalt compositions of the present invention may include less than 1%, in other embodiments less than 0.5%, in other embodiments less than 0.1%, and in other embodiments less than 0.05% by weight of an organophosphorous compound. In these or other embodiments, the asphalt compositions of the present invention are substantially devoid of organophosphorous compounds, where substantially devoid refers to that amount or less of organophosphorous compound that does not have an appreciable impact on the composition. Organophosphorous compounds include those disclosed in U.S. Pat. Nos. 5,990,206 and 6,024,788, which are incorporated herein by reference.

In one or more embodiments, the modified asphalt binder compositions of this invention can be prepared by introducing asphalt binder with a desired amount of polymer (e.g., unsaturated polymer) and organothionating agents at a desired temperature. In one embodiment, the polymer and organothionating agent may be added to molten asphalt binder at temperatures greater than about 120° C., or in other embodiments from about 140° C. to about 210° C. In one or more embodiments, the organothionating agents, polymer, and asphalt may be mixed or blended after or during introduction of the same. Mixing may then be continued for about 25 to about 400 minutes at a temperature of about 145° C. to about 205° C. (or in other embodiments from about 160° C. to about 193° C.). In one or more embodiments, the mixture of the asphalt binder, polymer, and organothionating agents may be sheared in order to disperse the polymer quickly into the asphalt. Shearing may be accomplished, for example, within a high shear mill such as that produced by Siefer. In other embodiments, simple low shear mixing may be employed where time is less important. In one or more embodiments, the resulting modified asphalt binder of the composition is a homogeneous mixture, which is a mixture where less than 1% by weight of polymer separates from the asphalt at 2° C. as determined by ASTM D-7173.

In one or more embodiments, the organothionating agents may advantageously be added to the asphalt binder composition together with (i.e., simultaneously with) the polymer. In other words, the organothionating agents need not be premixed into the asphalt binder prior to addition of the polymer. Likewise, the polymer need not be premixed into the asphalt binder composition prior to addition of the organothionating agents.

In one or more embodiments, the organothionating agents and polymer may be added directly to the asphalt binder (e.g., molten asphalt binder) without preblending the organothionating agents and unsaturated polymer together. The organothionating agents and polymer may be added simultaneously or sequentially to the asphalt binder. In one or more embodiments, where the organothionating agents and polymer are added to the same binder composition, the organothionating agents may be added first, followed by the polymer. In other embodiments, the polymer may be added to the asphalt binder first, followed by addition of the organothionating agents.

In yet other embodiments, the organothionating agents and unsaturated polymer may be separately introduced to and mixed with separate asphalt binder compositions, and then the individual binder compositions may be subsequently introduced and blended. For example, organothionating agents may be added to a first asphalt binder composition to form a first masterbatch binder composition. Likewise, polymer may be added to a second asphalt binder composition to form a second masterbatch binder composition. The first and second masterbatch compositions may then be introduced and blended with each other to form a modified asphalt binder composition according to the present invention.

In one or more embodiments, the present invention provides a method whereby a concentrate of organothionating agents and asphalt binder is introduced and blended with a concentrate of polymer and asphalt binder. This method advantageously allows for the efficient transport and/or storage of the organothionating agents compositions and/or polymer asphalt binder compositions. In other words, it has been advantageously discovered that by not introducing and combining the polymer, organothionating agents, and asphalt binder, higher concentrations of the organothionating agents and/or polymer within an asphalt binder composition can be achieved so long as the organothionating agents and unsaturated polymer are introduced and mixed into separate binder concentrates. Advantageously, the concentrates can be shipped to more regional locations where they can be introduced and blended with each other, and/or they can be advantageously diluted with additional asphalt binder at the regional locations.

In one or more embodiments, the organothionating agents-binder concentrate can include greater than 0.5 parts by weight, in other embodiments greater than 2.0 parts by weight, in other embodiments greater than 5.0 parts by weight, and in other embodiments greater than 8.0 parts by weight organothionating agents per 100 parts by weight asphalt. In these or other embodiments, the organothionating agents-binder concentrate can include up to 10 parts by weight, and in other embodiments up to 12 parts by weight organothionating agents per 100 parts by weight asphalt binder. Those skilled in the art appreciate that the ability to process and handle the asphalt (e.g., pumpability per AASHTO T316) may dictate the upper levels of organothionating agents that can be added to an asphalt binder.

Similarly, the polymer-binder concentrate can include greater than 5 parts by weight, in other embodiments greater than 10 parts by weight, in other embodiments greater than 15 parts by weight, and in other embodiments greater than 18 parts by weight polymer per 100 parts by weight asphalt. In these or other embodiments, the polymer-binder concentrate can include up to 20 parts by weight, in other embodiments up to 25 parts by weight, and in other embodiments up to 30 parts by weight polymer per 100 parts by weight asphalt binder. Those skilled in the art appreciate that the ability to process and handle the asphalt (e.g., pumpability per AASHTO T316) may dictate the upper levels of polymer that can be added to an asphalt binder. Other factors that may impact the upper limit of polymer concentration include polymer molecular weight, polymer macrostructure, and characteristics of the asphalt.

In one or more embodiments, the asphalt employed to prepare the organothionating agents-binder concentrate may have different characteristics than the asphalt employed to make the polymer-binder concentrate. For example, in one embodiment, the asphalt employed to prepare the polymer-binder concentrate may be a softer asphalt than is used to prepare the organothionating agents-binder concentrate. This may be advantageous because greater loadings of polymer can be added to softer asphalt, thereby providing the ability to transport and/or store more polymer with less asphalt. Also, by preparing the organothionating agents-binder concentrate and polymer-binder concentrate with distinct asphalt, desirable properties can be achieved upon blending. For example, the organothionating agents-binder concentrate can be prepared with a relatively hard asphalt, which when blended with the polymer-binder concentrate made with a relatively soft asphalt, a hardness between the asphalt binders employed to make the concentrates can be achieved.

One particular embodiment of the method according to the present invention is shown in FIG. 1. A storage container of organothionating agents 22, a storage container of asphalt binder 24, and a storage container of unsaturated polymer 26 can be located at a modified asphalt binder facility 12. An organothionating agent-binder concentrate 28 can be formed by introducing and blending thionating agents and asphalt binder. The step of introducing and blending can be achieved by adding particulate organothionating agents to an asphalt binder composition maintained at a temperature of from about 120° C. to about 205° C. Likewise, an unsaturated polymer-binder concentrate 30 can be prepared by introducing and mixing unsaturated polymer with asphalt binder. The introduction and mixing of the unsaturated polymer and binder can be achieved by adding pellets of unsaturated polymer to a molten asphalt binder composition maintained at a temperature of from about 120° C. to about 205° C. The respective asphalt binder concentrates (i.e., concentrate 28 and concentrate 30) can then be shipped to a terminal 14. The shipping of the concentrates can occur by heated or insulated freight carrier. Advantageously, these concentrates can be shipped via insulated freight carrier to terminal 14 located up to and in excess of 1,000 miles from the modified asphalt binder facility 12.

At terminal location 14, the organothionating agents-binder concentrate and the unsaturated polymer-binder concentrate can be introduced and blended. This introduction and blending can occur at temperatures at about 145° C. to about 170° C. Also, the concentrates, before or after their introduction and blending, can be diluted with additional asphalt binder, which can be stored at terminal 14 within container 32. The modified binder 34, which is diluted to a desired level of organothionating agents and/or unsaturated polymer as provided herein, may then be transported to a hot-mix plant 16. Transportation of this modified asphalt binder composition may occur within a heated or insulated freight container and can be shipped up to and in excess of 300 miles to hot-mix plant 16.

At hot-mix plant 16, the modified binder composition can be introduced and mixed with aggregate 36 to form paving composition 38. Methods for introducing and mixing aggregate and modified binder composition are known in the art and include batch mixing and continuous mixing. In one or more embodiments, the aggregate and modified asphalt binder are introduced and mixed by first preheating the modified asphalt binder to a temperature of about 120° C. to about 200° C. Once the paving composition 38 has been prepared, the paving composition can be transported to a job site (e.g., road bed) where pavement can be paved. Transportation of the paving composition can occur within a heated or insulated freight carrier.

The modified asphalt binder compositions prepared according to the present invention may be employed to prepare asphalt paving compositions. These paving compositions may include the modified asphalt binder, aggregate, and other optional constituents that can be added into paving compositions as is known in the art. Conventional aggregate that is used in the paving industry can be utilized in the practice of this embodiment. Aggregate may include rocks, stones, slags, crushed stone, gravel, sand, silica, or mixtures of one more thereof. Specific examples of aggregates include marble, limestone, basalt, dolomite, sandstone, granite, quartzite, steel slag, and mixture of two or more thereof.

Aggregate typically has a wide distribution of particle sizes ranging from sub-micron particles (e.g., dust) to golf-ball sized masses as large as 63 mm in diameter. The best particle size distribution varies from application to application.

In addition to the aggregate and the modified asphalt binder, the paving compositions of the present invention may also include other constituents or ingredients that may be used in preparing asphalt paving compositions. These additional constituents or ingredients may include fibers, release agents, and fillers. Other examples include calcium hydroxide, sanders dust, cellulose fibers, propylene-based fibers, and mixtures of two or more thereof.

The asphalt paving compositions of the present invention can be prepared by using standard equipment and procedures. In one or more embodiments, the aggregate is mixed with the modified asphalt binder to attain an essentially homogeneous asphalt paving. For instance, the aggregate can be mixed with the modified asphalt binder to produce asphalt paving composition on a continuous basis in a standard mixer. In one or more embodiments, practice of the present invention advantageously eliminates the need to treat the aggregate prior to formation of the asphalt concrete.

When preparing an asphalt paving composition, generally from about 1 weight percent to about 10 weight percent of the modified asphalt and from about 90 weight percent to about 99 weight percent aggregate (based on the total weight of the asphalt paving composition) is mixed. In other embodiments, the paving compositions include from about 2 to about 8 weight percent of the modified asphalt.

The asphalt binder compositions, as well as the asphalt paving compositions, prepared according to the present invention demonstrate several advantageous properties. In one or more embodiments, the compositions may advantageously be stored at elevated temperatures without deleteriously impacting the separation point of polymer and asphalt binder.

The asphalt paving compositions prepared according to the present invention are particularly advantageous for preparing pavements. These pavements may include, but are not limited to, roadway, airport runways, walkways, trails, golf cart paths, pond liner, landfill covers, and bridge decks. Also, the modified asphalt binder compositions of the present invention are advantageous for making other compositions besides the pavement compositions. For example, the modified asphalt compositions may be useful in roofing applications.

In order to demonstrate the practice of the present invention, the following examples have been prepared and tested. The examples should not, however, be viewed as limiting the scope of the invention. The claims will serve to define the invention.

Examples

Samples 1-6

Asphalt binder compositions were prepared by employing the following method. To a quart can container was added 500 grams of asphalt binder preheated to 163° C. The asphalt binder was obtained from BP (Whiting, Ind.) and had a PG rating of 64-22 per AASHTO M320. Using a quart can heater, the asphalt binder was heated to 190° C. and rotated on a Silverson high shear mixer at which time was added particulate Lawesson's Reagent by direct addition of the particulate to the asphalt binder and pellets of unsaturated polymer by direct addition of the pellets to the asphalt binder. Shearing of the sample within the container continued for 30 minutes. A lid was loosely placed on the container, and the container was placed in an oven set at 163° C. for 18 hours. Upon removal of the container from the oven, and removal of the lid, any skim layer present was removed. The sample was then stirred and poured through a 20 mesh screen, and the screened material was used for preparing test samples.

The amount of modifier (e.g. Lawesson's Reagent and unsaturated polymer) added to each sample is set forth in Table I. A portion of each sample was taken and prepared into various test specimens as required for each standardized test employed. The test methods employed throughout these Examples are provided in Table I.

The unsaturated polymer employed in this set of Samples was a radial polymer that was characterized by about 16.5% vinyl, was 90% tetra-coupled, included about 30% block styrene, had a base peak molecular weight ($M_p$) of about 53 kg/mole, and an $M_p$ after coupling of about 228 kg/mole; this polymer was obtained under the tradename 161-B™ (LCY; China).

The amount of unsaturated polymer and Lawesson's Reagent are provided in Table I in parts by weight per 100 parts by weight asphalt (pha). Note that Sample 1 is a control and does not include Lawesson's Reagent or unsaturated polymer, and Sample 2 includes polymer but no Lawesson's Reagent and is therefore also a useful control.

Various modifications and alterations that do not depart from the scope and spirit of this invention will become apparent to those skilled in the art. This invention is not to be duly limited to the illustrative embodiments set forth herein.

What is claimed is:

1. A process for preparing a modified asphalt binder composition, the process comprising:

mixing asphalt, an unsaturated polymer, and an organothionating agent to form a modified asphalt composition, where the organothionating agent is defined by the formula

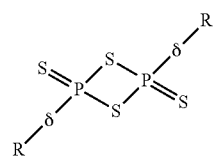

where each R is independently a monovalent organic group and each δ is independently a bond or a heteroatom, or where the organothionating agent is defined by the formula

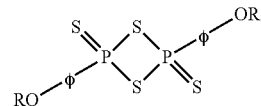

where φ is a phenyl group or substituted phenyl group and R is a monovalent organic group.

2. A process for preparing a modified asphalt binder composition the process comprising:

introducing an polymer to an asphalt binder; and introducing an organothionating agent to an asphalt binder, where said step of introducing organothionating agents to the asphalt includes adding an organothionating agent composition that includes less 5% by weight hydrocarbon material, where the organothionating agent is defined by the formula

TABLE I

| Samples | TEST Method | 1 | 2 | 3 | 4 | 5 | 6 |
| --- | --- | --- | --- | --- | --- | --- | --- |
| Modifier (parts per 100 asphalt) | | — | | — | — | — | — |
| Unsaturated Polymer | | — | 1.25 | — | 1.5 | 1.5 | 1.5 |
| Lawesson's Reagent | | — | — | 1.0 | 0.5 | 0.5 | 1.0 |
| Sulfur | | — | — | — | — | 0.1 | — |
| Performance Analysis | | — | — | — | — | — | — |
| Original DSR Fail Temp. (° C.) | AASHTO T315 | 65.5 | 69.0 | 68.8 | 74.1 | 74.5 | 76.7 |
| RTFO DSR Fail Temp. (° C.) | AASHTO T240/T315 | 65.6 | 69.0 | 69.8 | 73.5 | 73.0 | 75.3 |
| Phase Angle @ 76° C. | AASHTO T315 | 89.0 | 87.4 | — | — | 73.2 | 70.7 |
| Elastic Recovery @ 25° C. (%) | AASHTO T301 | 24.0 | 44.0 | — | 77.5 | 82.0 | 86.0 |
| Separation (° C.) | ASTM D-7173 | 0.3 | 0.5 | — | 0 | 2 | 2 |
| Softening Point (° C.) | AASHTO T53 | 48.1 | 52.2 | 125 | 137 | 142 | 148 |

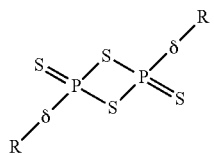

where each R is independently a monovalent organic group and each δ is independently a bond or a heteroatom, or where the organothionating agent is defined by the formula

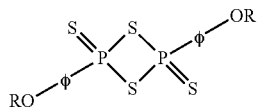

where φ is a phenyl group or substituted phenyl group and R is a monovalent organic group.

3. A method for forming a modified asphalt binder composition, the method comprising:
preparing an organothionating agent-binder concentrate by introducing and mixing organothionating agent and asphalt binder, where the organothionating agent-binder concentrate includes greater than 0.5 parts by weight organothionating agents per 100 parts by weight asphalt;
preparing a polymer-binder concentrate by introducing and mixing polymer and asphalt binder, where the polymer-binder concentrate includes greater than 5 parts by weight polymer per 100 parts by weight asphalt; and
introducing and mixing the organothionating agent-binder concentrate with the polymer-binder concentrate to form a modified asphalt binder composition, where the organothionating agent is defined by the formula

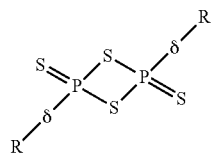

where each R is independently a monovalent organic group and each δ is independently a bond or a heteroatom, or where the organothionating agent is defined by the formula

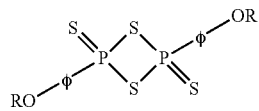

where φ is a phenyl group or substituted phenyl group and R is a monovalent organic group.

4. The process of claim 1, where at least one R is an aryl group.

5. The process of claim 4, where each R is independently an aryl group.

6. The process of claim 1, where the organothionating agent is the Lawesson's Reagent.

7. The process of claim 1, where the binder includes from about 0.02 to about 5 parts by weight organothionating agent per 100 parts by weight binder.

8. The process of claim 1, where the weight ratio of polymer to the organothionating agent is at least 0.5:1 and less than 8:1.

9. The process of claim 1, further comprising the step of mixing the modified asphalt binder composition.

* * * * *